US007728296B2

(12) United States Patent
Cole et al.

(10) Patent No.: US 7,728,296 B2
(45) Date of Patent: Jun. 1, 2010

(54) SPECTROSCOPY APPARATUS AND ASSOCIATED TECHNIQUE

(75) Inventors: Bryan E. Cole, Cambridgeshire (GB); Michael C. Kemp, Cambridgeshire (GB); William R. Tribe, Cambridgeshire (GB); Philip F. Taday, Cambridgeshire (GB)

(73) Assignee: TeraView Limited, Cambridge (GB)

( * ) Notice: Subject to any disclaimer, the term of this patent is extended or adjusted under 35 U.S.C. 154(b) by 0 days.

(21) Appl. No.: 10/550,183

(22) PCT Filed: Mar. 19, 2004

(86) PCT No.: PCT/GB2004/001194

§ 371 (c)(1),
(2), (4) Date: Jun. 6, 2006

(87) PCT Pub. No.: WO2004/083796

PCT Pub. Date: Sep. 30, 2004

(65) Prior Publication Data

US 2006/0255277 A1    Nov. 16, 2006

(30) Foreign Application Priority Data

Mar. 21, 2003   (GB)   ................................. 0306586.9

(51) Int. Cl.
*G01N 21/35* (2006.01)
(52) U.S. Cl. .................................................. 250/338.1
(58) Field of Classification Search ............... 250/338.1
See application file for complete search history.

(56) References Cited

U.S. PATENT DOCUMENTS

| 5,623,145 | A | * | 4/1997 | Nuss ........................ 250/330 |
| RE36,201 | E | * | 4/1999 | Miller .................. 250/390.04 |
| 6,078,047 | A | * | 6/2000 | Mittleman et al. ....... 250/338.1 |
| 6,480,141 | B1 | * | 11/2002 | Toth et al. ..................... 342/22 |
| 6,605,808 | B2 | * | 8/2003 | Mickan et al. ........... 250/341.8 |
| 2001/0033636 | A1 | | 10/2001 | Hartick et al. |
| 2005/0082479 | A1 | * | 4/2005 | Wallace et al. ............. 250/330 |
| 2006/0022140 | A1 | * | 2/2006 | Connelly et al. ......... 250/338.1 |

FOREIGN PATENT DOCUMENTS

WO    WO 00/50859    8/2000
WO    WO 02/057750    7/2002

OTHER PUBLICATIONS

Mittleman, et al., "T-Ray Imaging" IEEE Journal of Selected Topics in Quantum Electronics, IEEE Service Center, US, vol. 2, No. 3, pp. 679-692, Sep. 1, 1996.

* cited by examiner

*Primary Examiner*—David P Porta
*Assistant Examiner*—Marcus H Taningco
(74) *Attorney, Agent, or Firm*—Dickstein Shapiro LLP

(57) ABSTRACT

Apparatus and method for detecting an explosive material, involving irradiating an object with a continuous wave (CW) or pulsed beam of Terahertz radiation, preferably in the frequency range of 100 GHz to 100 THz and detecting radiation transmitted and/or reflected from the object. A spectrum is constructed from the detected radiation, which is indicative of a fundamental property of the explosive material. This constructed spectrum is compared with one or more known spectra of explosive materials to determine whether a likeness exists.

20 Claims, 14 Drawing Sheets

SPECTROSCOPY APPARATUS AND ASSOCIATED TECHNIQUE

The present invention relates generally to the field of apparatus and methods for imaging and/or investigating samples in the far-infrared (far-IR)/Terahertz (THz) frequency range. More specifically, the present invention relates to investigating a sample containing an explosive material and obtaining a spectral signature of the sample using radiation in the far-infrared/Terahertz frequency range from 100 GHz to 100 THz. Preferably the radiation utilised is in the frequency range of 500 GHz to 100 THz and more preferably from 1 THz to 100 THz and most preferably from 700 GHz to 10 THz.

It is well established that many chemicals and pharmaceutical agents have spectral signatures in the THz region. The reason for the spectral signals in this frequency range is considered to be associated with inter-molecular or intra-molecular crystalline vibrations or collective phonon oscillations. It is known that in THz spectroscopy the spectral information of transmitted and/or scattered radiation can be used to identify materials. Most materials interact with terahertz waves to some degree, and each material has its own frequency pattern, which can be considered as a kind of 'fingerprint'.

Of late security concerns have increased the need for a system that is able to identify hidden explosives, such as under a person's clothing, in a person's suitcase or in a postal package.

US Patent Application No. 2001/0033636 discloses a method of detecting explosives in luggage which uses X-rays to determine an average atomic number of a material. The average atomic number is then compared with known average atomic numbers of explosive materials to determine if the material being examined is an explosive. This technique, however is unsuitable for routine-security screening of people as its radiation is ionising.

In a paper entitled "Spectroscopy with electronic terahertz techniques" by D. W. van der Weide et al published in Proc Spie 3828 (99), electronic pulses in the microwave range, up to 450 GHz, are used to investigate explosives. These pulses are generated electronically using non-linear transmission lines, coupled with varactor diodes that are patterned on a semiconductor. A sine wave is applied to the transmission line and the result at the other end is a rapid (1-2 ps) voltage step, which is used to produce the microwave pulse from the semiconductor device. This paper demonstrates spectral features of explosives, but only in the sub-terahertz or microwave frequency range.

Several reflection spectra are illustrated in the paper up to 450 GHz and it is stated that the contrast in the spectra between the different materials probably arises from the granularity of the materials, their dielectric constants and orientation of the sample. Granularity and orientation are both features that are alterable when creating an explosive material. Therefore, if an explosive detector is based on the detection of spectral features dependent on granularity and orientation, explosives could be altered so that the spectral features being identified were masked. This could result in the explosive material passing through the explosive detector unnoticed.

There is therefore a need for a technique of identifying explosive materials that is not dependent upon alterable spectral features.

THz radiation is suitable for screening people and their possessions as it is non-ionising and can pass through clothing, paper, cardboard, wood, masonry, plastic and ceramics. Therefore, it is safer than x-ray techniques.

It has been speculated that THz radiation could be used to obtain spectral information of explosive materials, as the organic molecular nature of explosives, and their crystalline structure are of the appropriate form. To date, however, this has not been effectively achieved.

There is therefore also a need for a technique for imaging and/or investigating explosive materials using THz radiation.

One of the problems that needs to be overcome, however, in devising a suitable technique of investigating explosives using THz radiation, is the ability to distinguish explosives from surrounding materials. For example, it is desirable to be able to distinguish plastics explosives from the molecular structure of suitcases or clothing and the like.

It is therefore an aim of the present invention to overcome or alleviate at least one of the problems of the prior art.

According to one aspect the present invention provides a method of detecting an explosive material or composition, comprising:

irradiating an object with an optically-generated pulse of electromagnetic radiation, said pulse having a plurality of frequencies in the range from 100 GHz to 100 THz;

detecting radiation transmitted and/or reflected from the object; and identifying one or more features of the detected radiation which are indicative of a known explosive material or composition.

Preferably the analysis of the detected radiation comprises determining a frequency spectrum from the detected radiation.

This aspect of the invention utilises an optical technique which permits access to high frequency spectral regions where there are unique and intrinsic spectral identifiers, whilst also permitting assessment of lower frequency features.

This aspect of the invention preferably uses a laser to drive emitting and detecting devices. Laser pulses are much shorter than those which can be generated by electronic means (<200 fs compared with 1-2 ps). In this way the apparatus has a larger usable frequency range than systems based on electronic methods, and accesses higher THz frequencies as well as the lower frequency band (a typical range being 0.1-4 THz as compared to 0-450 GHz for electronic generation means). It has been found that the higher frequencies accessed via the present invention enables unique features relating to fundamental properties to be extracted from the spectral signatures of explosive materials, aiding in uniquely identifying these materials.

According to a further aspect there is provided a method of detecting an explosive material, comprising:

irradiating an object with an optically-generated beam of substantially continuous electromagnetic radiation having a frequency in the range 100 GHz to 100 THz;

detecting radiation transmitted and/or reflected from the object;

analysing the detected radiation to determine if one or more predetermined features of an explosive material exists.

This further aspect of the invention is a CW (Continuous Wave) technique. CW techniques involve the illumination of devices, but this time with multiple CW laser sources, producing an output frequency in the THz band at the difference frequency. As with pulsed techniques, higher frequencies can be achieved than by electronic methods. Furthermore, CW techniques are advantageous (whether optical or electronic), as they can more easily handle arbitrary target distances.

Preferably this CW technique also comprises determining whether a reference beam at the detector is in phase with the detected radiation and adjusting a delay line by at most ½ a period of the detected radiation to achieve an in-phase.

Therefore, advantageously this CW technique can readily account for arbitrary changes in the THz path length to the detector.

Preferably the analysis of the detected radiation utilising the CW technique comprises obtaining a frequency spectrum at a number of predetermined frequencies and analysing the spectra at the predetermined frequencies to determine if features of known explosive materials are present. In this regard, CW radiation is tunable but monochromatic, which it has been found allows discrete measurements to be made at predetermined key indicative frequencies.

Preferably the analysis of the detected radiation in these aspects of the invention comprises determining whether the detected radiation is indicative of a fundamental property of the explosive material.

Where the explosive material or composition is covered with a member, such as hidden in a bag or suitcase or under a person's clothing, the technique of the present invention may also involve compensating for the signal due to the member by differentiating the detected radiation. For instance, the signal may be compensated for by obtaining the first derivative of a frequency spectrum of the detected radiation.

Advantageously, it has been found that where the detection technique is undertaken in relation to detecting explosive materials hidden under clothing or the like, the contribution to the spectra from clothing can be essentially eliminated by determining the first derivative spectra. Hence this feature can allow a spectrum of an explosive material to be accurately obtained.

According to another aspect the present invention provides a method of detecting an explosive material or composition, comprising:

irradiating an object with an optically-generated pulse of electromagnetic radiation, said pulse having a plurality of frequencies in the range from 100 GHz to 100 THz;

detecting radiation transmitted and/or reflected from the object; and analysing the detected radiation to determine if one or more predetermined features of an explosive material exists.

Where the analysis comprises determining a frequency spectrum from the detected radiation, preferably the method of both aspects of the invention further comprise obtaining a first derivative of the obtained spectra.

It has been found that the optical techniques utilised in these aspects of the invention enable the identification of unique spectral signatures of explosive materials, regardless of their orientation or material structure.

Preferably, where a frequency spectrum is obtained it is an absorption spectrum or a reflection spectrum. It is also preferable that analysis of the detected radiation further comprises analysing the frequency spectrum at predetermined frequencies to determine if features of known explosive materials/compositions are present. This analysis may involve comparing the spectral intensity at the predetermined frequencies with expected intensities relating to one or more explosive materials/compositions.

As mentioned above, it is well established that many chemicals and pharmaceutical agents have spectral signatures in the THz region. Since each spectral signature is unique, the ratios of absorption intensity at a distinct set of frequencies are also unique and can be used in identification. As an alternative to the analysis method above therefore, the analysis may involve calculating at least one ratio of absorption intensity at first and second predetermined frequencies and comparing with expected intensity ratios relating to one or more explosive materials. Preferably, in such analysis a plurality of intensity ratios are calculated for the spectral signature from a predetermined set of frequencies.

Analysis of the spectral information by calculating ratios of absorption intensities is suitable for both pulsed and CW imaging. However, it is particularly advantageous where imaging is only possible at a limited number of discrete frequencies (as opposed to imaging across the whole frequency range of interest).

One or more of the predetermined frequencies may be selected to correspond to a feature indicative of a fundamental property of an explosive material as well as corresponding to a region of low atmospheric water absorption. Alternatively, or in addition, measures may be applied to reduce water absorption effects in the detected radiation. For example, the effects of water absorption may be reduced by reducing the resolution in the analysis of the detected radiation.

According to an additional aspect, the present invention provides a method of detecting an explosive material or composition, comprising:

irradiating an object with a pulse of electromagnetic radiation, said pulse having a plurality of frequencies in the range from 500 GHz to 100 THz;

detecting radiation transmitted and/or reflected from the object; and analysing the detected radiation to determine if one or more predetermined features of an explosive material exists.

This aspect of the invention does not require the pulse to be optically generated, provided high frequency spectral regions are achievable, where there are unique and intrinsic spectral identifiers.

In another aspect, the present invention provides an explosive detection apparatus, comprising:

an optically-driven emitter for irradiating an object with a beam of substantially continuous electromagnetic radiation having a frequency in the range 100 GHz to 100 THz;

means for detecting radiation transmitted and/or reflected from the object, analyser for analysing the detected radiation to determine if one or more predetermined features of an explosive material exists.

This aspect of the invention provides a detection apparatus that operates using continuous wave radiation.

In a further aspect, the present invention provides an explosive detection apparatus, comprising:

an optically-driven emitter for irradiating an object with a pulse of electromagnetic radiation, said pulse having a plurality of frequencies in the range from 100 GHz to 100 THz;

means for detecting radiation transmitted and/or reflected from the object;

analyser for analysing the detected radiation to determine if one or more predetermined features of an explosive material exists.

This aspect of the invention operates using pulsed radiation. Preferably the analyser in this apparatus, and the CW apparatus, calculates a frequency spectrum from the detected radiation. It is also preferable that the apparatuses further comprises a comparator for comparing the calculated spectrum with one or more known spectra of explosive materials or compositions to determine whether a likeness exists. Preferably the known features are indicative of a fundamental property of the explosive material.

The present invention is directed towards apparatus and methods for detecting explosive materials or compositions, which includes explosive materials in their pure form or combined with other materials, such as other explosives or plasticisers. It also includes explosive materials or compositions in any form including solid, liquid or gaseous form.

The detection apparatus may be incorporated in a hand held unit, such as a probe or wand, for detecting and identifying explosives hidden on people, in packages, in bags etc. Such a unit would preferably utilise reflectance spectra. The detection apparatus may also be configured in a belt-type scanner for detecting explosives in letters, parcels, packages, bags, luggage etc. Further, the detection apparatus may be incorporated in a walk-through portal for screening people and large objects for explosives. Another application for this detection apparatus is in a stand-off or camera/telescope type system for detecting explosives at a distance, for example to locate suicide bombers and suspected bombs in a large area.

According to a still further aspect, the present invention provides the use of Terahertz radiation in the detection of explosive materials.

Preferably in these aspects of the invention the radiation irradiating the object is in the Terahertz frequency range of 500 GHz to 100 THz, particularly in the range of 1 THz to 100 THz and more particularly in the range of 700 GHz to 10 THz. It has been found that investigating in these frequency ranges are most preferred, as the spectral features apparent at these higher frequencies are due to fundamental properties of the explosive materials, such as vibrational or phonon states of chemical bonds and molecules.

A further advantage of using THz radiation is that it has a shorter wavelength than microwaves and therefore provides better penetration (less scatter) than microwave and near-infrared wavelengths.

The present invention will now be described with reference to the accompanying drawings in which.

Figure 13:
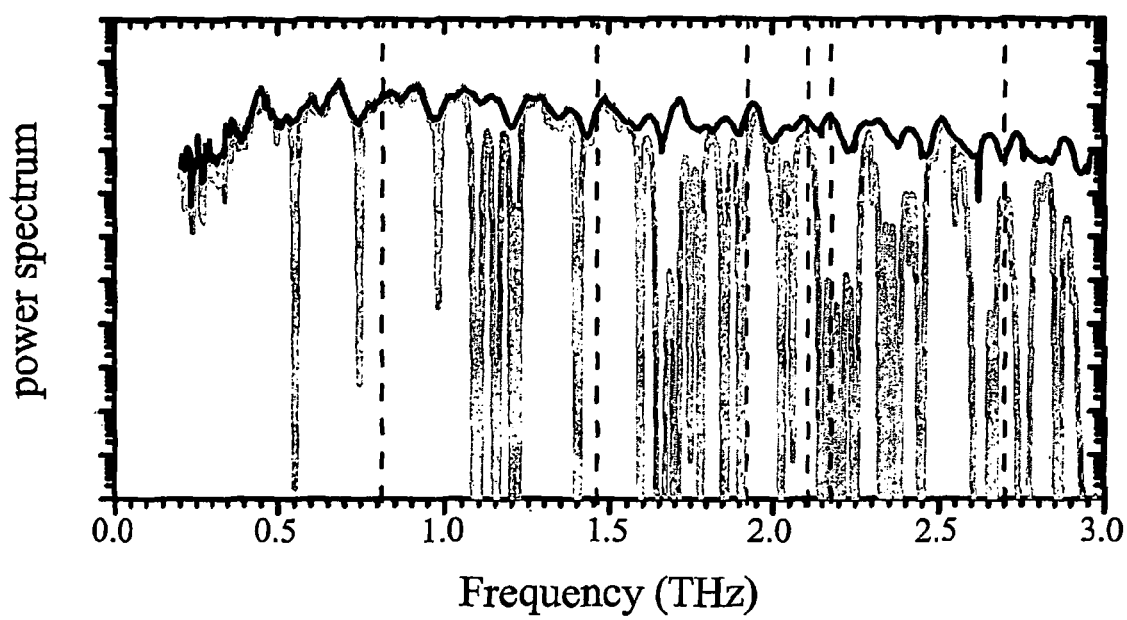
Figure 14:
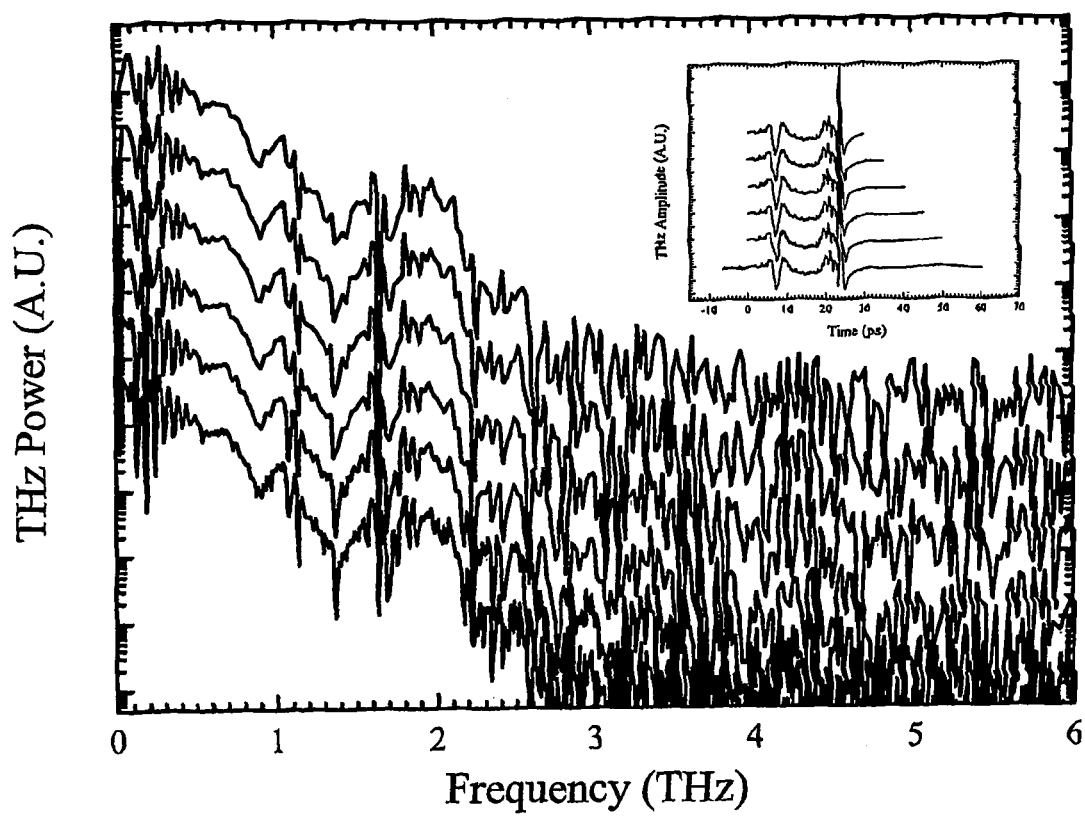

FIG. 13 compares a THz power spectrum measured in an evacuated environment with the corresponding THz power spectrum calculated to include passage through 5 m of air in normal atmospheric conditions; and FIG. 14 THz power spectra for PE-4 with varying resolutions.

Figure 1:
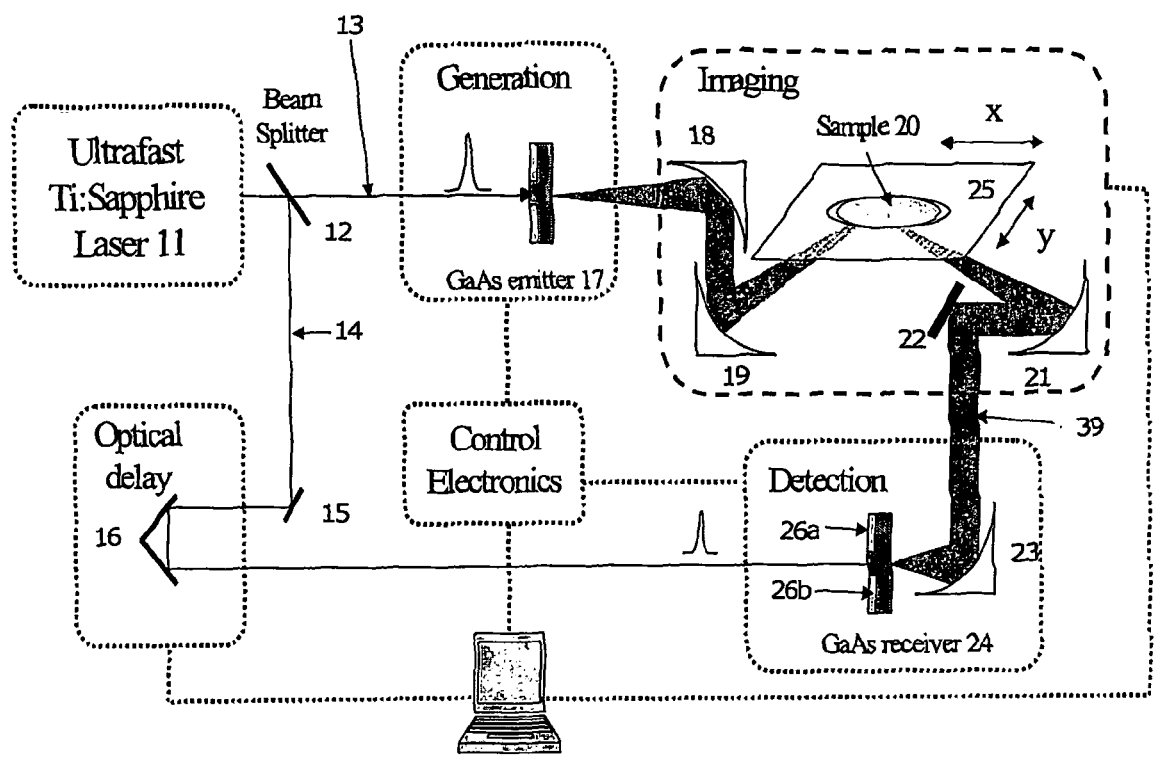
FIG. 1 illustrates a schematic of a pulsed terahertz reflection investigative technique utilised in a first embodiment of the present invention.
Figure 2:
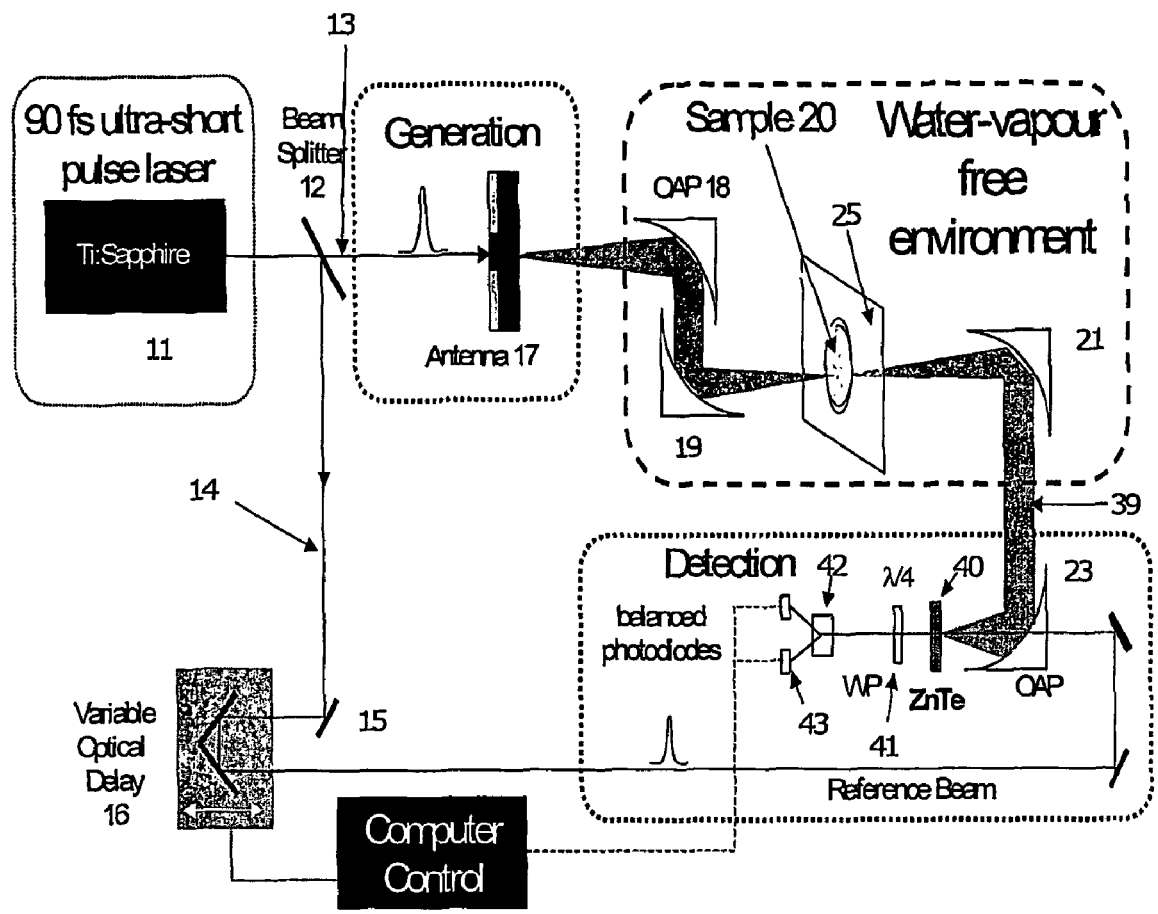
FIG. 2 illustrates a schematic of a pulsed terahertz transmission investigative technique utilised in a second embodiment of the present invention.
Figure 3:
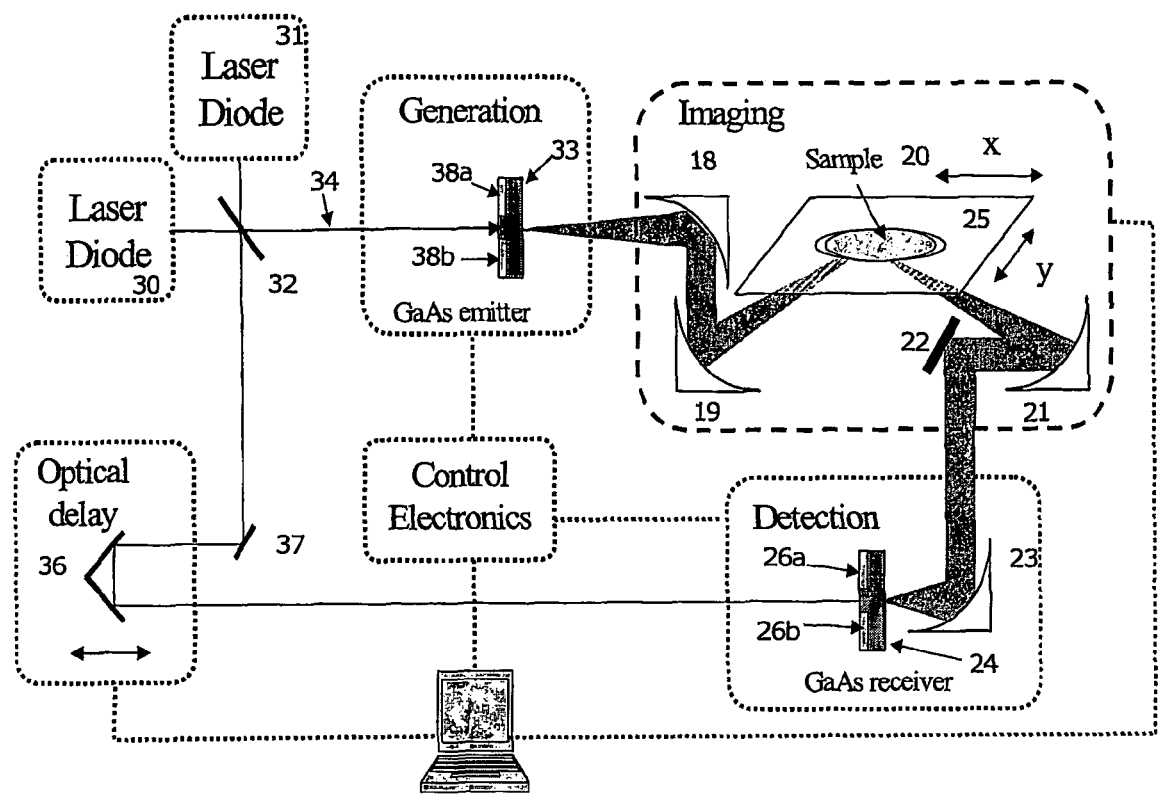
FIG. 3 illustrates a schematic of a continuous wave terahertz investigative technique utilised in a third embodiment of the present invention.

FIGS. 1 to 3 illustrate three different terahertz investigating arrangements that may be adapted for use in an explosive detecting apparatus.

Referring to FIG. 1, a terahertz pulsed investigating arrangement is illustrated, which comprises an ultra-short pulse laser 11 which may be, for example, Ti:sapphire, Yb:Er doped fibre, Cr:LiSAF, Yb:silica, Nd:YLF, Nd:Glass, Nd:YAG, Alexandrite Yb:Phosphate Glass QX, Yb:GdCOB, Yb:YAG, Yb:KG d(WO$_4$) or Yb:BOYS laser. This laser 11 emits pulses of radiation 13, such as a collimated beam of pulses, each of which comprise a plurality of frequencies. The pulses generated by the laser preferably having a pulse duration of less than 200 fs.

The beam of generated pulses is directed into beam splitter 12. The beam splitter splits the beam into a pump beam 13, which is used to irradiate the sample, and a probe beam 14, which is used during detection.

The probe beam 14 is directed, via plain mirror 15, into scanning delay line 16. Scanning delay line 16 is a variable optical delay, which in its simplest form comprises two mirrors that serve to reflect the beam through a 180° angle. Using a computer as a controller, these mirrors can be quickly swept backwards and forwards in order to vary the path length of the probe beam 14. In this way the scanning delay line 16 assists in matching the relative path lengths of the pump and probe beams. The probe beam is then focussed onto receiver 24 for combining with the Terahertz beam.

The pump beam 13 is directed onto a source 17. For pulsed approaches this source 17 preferably comprises a GaAs based photoconductive switch. GasAs based devices use the principle of photoconductive mixing to generate their THz output.

The radiation emitted by the emitter 17 is directed via a hyper-hemispherical lens (not shown) towards a first parabolic mirror 18, which is preferably an off axis parabolic (OAP) mirror, as are all the parabolic mirrors referred to herein. The beam is then reflected off the first parabolic mirror 18 and onto second parabolic mirror 19, which directs the radiation onto sample 20.

To analyse a particular sample in situ, the sample 20 may be moved relative to the beam of radiation through the focal plane of the THz beam or the beam may be moved relative to the sample or both. As shown in FIG. 1, the sample may be placed on a translation stage 25 to appropriately move the sample. This translation stage 25 could move the sample one dimensionally along one axis of movement or through two or three axes of movement.

The THz radiation that is reflected from sample 20 is collected by third parabolic mirror 21 and onto a fourth parabolic mirror 23 via plain mirror 22. The fourth parabolic mirror 23 directs the reflected radiation onto a second hyper-hemispherical lens (not shown) and onto a detector 24, such as an electro-optic detector or a photoconductive detector.

Photoconductive detectors comprise a detection member which may be, for example, GaAs, InGaAs, Si on Sapphire etc. The detection member 24 is used to detect both the amplitude and phase of the radiation emitted from the sample 20. In these detectors, the THz radiation 39 from the sample is incident on the back surface of the detection member 24. The radiation is collected by a lens (not shown), which may be hemispherical or have another shape. The Terahertz radiation 39 incident on the detection member 24 induces a photocurrent through the region between electrodes 26a and 26b, located on the opposing side of the detection member 24, which is being illuminated by the laser radiation. As the detector needs to know information about the phase of the radiation emitted from the generator 17, the radiation illuminating the region between electrodes 26a and 26b is preferably the probe beam 14, which carries this information. The current that can then be detected by the electrodes is proportional to the strength of the THz field 39.

The electrodes 26a, 26b may be of a simple diode formation embedded in a transmission line. Alternatively, they may be triangular and arranged in the shape of a bow-tie to form a so-called bow-tie antenna. They may also be interdigitated electrodes at the centre of a bow-tie or spiral antenna.

FIG. 2 illustrates an alternative pulsed arrangement, whereby the sample is investigated using transmitted radiation rather than reflected radiation and the detector is an EOS detector rather than a photoconductive detector. To avoid unnecessary repetition with respect to FIG. 1, like reference numerals will be used to denote like features.

In FIG. 2, it is apparent that a variable delay is introduced to the probe beam 14 and that the pump beam 13 is projected onto the sample in the same manner as was illustrated in FIG. 1. The sample in FIG. 2, however is now generally perpendicular to the incident pump beam, in order to maximise radiation transmission.

Transmitted radiation 39 is combined with the probe beam 14. One particularly popular way to do this is to use electro-optic sampling (EOS). In this technique, the transmitted THz beam 39 and the probe beam 14 co-linearly propagate through an EOS detector 40. The transmitted radiation 39 passes through the detector 40, which modulates the probe beam 14.

The EOS detector 40 may be comprised of any material which possesses good non-linear characteristics, such as GaAs or Si based semiconductors and $NH_4H_2PO_4$, ADP, $KH_2PO_4$, $KH_2ASO_4$, Quartz, $AlPO_4$, ZnO, CdS, GaP, $BaTiO_3$, $LiTaO_3$, $LiNbO_3$, Te, Se, ZnTe, ZnSe, $Ba_2NaNb_5O_{15}$, $AgAsS_3$, proustite, CdSe, $CdGeAs_2$, $AgGaSe_2$, $AgSbS_3$, ZnS, organic crystals such as DAST (4-N-methylstilbazolium).

The modulated beam is then passed into quarter wave plate 41. This serves to circularly polarise the emitted radiation. The circularly polarised light is then fed through a Wollaston prism 42, which divides the polarization of the light onto two orthogonal components. These two orthogonal components are then directed onto balanced photodiode assembly 43. The balanced photodiode assembly comprises two photo diodes to respectively detect each of the orthogonal components from the Wollaston prism 42. The output of the photodiodes are then linked together such that the balanced photodiode assembly 43 only outputs an electrical signal if there is a difference between the readings of the two photodiodes. This output signal corresponds to the strength of the transmitted THz beam 39, This is because, where there is no THz beam present, there is no difference between the two photodiode signals. However, where there is a THz beam 39, the THz beam 39 serves to make the radiation exiting the detector 40 slightly elliptically polarised. This change in the polarization still remains after the radiation is passed through quarter waveplate 41. Extracting the orthogonal components of this radiation using prism 42 causes a different signal to be measured at the two photodiodes, and hence balanced photodiode assembly 43 outputs a signal corresponding to the strength of the THz field.

Therefore EOS detection enables the phase and amplitude of the transmitted radiation to be detected. It is to be appreciated that it will be apparent to those skilled in the art that this type of analysis could be performed for any type of detector.

It is also to be appreciated that it is also possible to combine the arrangements of FIGS. 1 and 2, whereby both reflected and transmitted radiation from the sample is measured.

Further, rather than combining the beam which has been reflected from or transmitted by the sample with the probe beam 14, it is also possible to combine the THz beam with another beam of radiation which has substantially the same wavelength or which differs in frequency by at most 10 GHz. Such combined radiation can be detected using a bolometer, Schottky diode etc.

While these apparatuses has been described in relation to pulses, such as a collimated beam of pulses, it is to be appreciated that the present invention may also be implemented using a continuous wave (CW) source. Continuous wave generation is described in detail in European patent application number 01907935.9.

FIG. 3 illustrates a CW Terahertz investigating arrangement. To avoid unnecessary repetition in relation to FIGS. 1 and 2, like reference numerals will be used to denote like features.

Two laser diodes 30, 31 are configured to emit radiation with frequencies $\omega_1$ and $\omega_2$ respectively. The radiation emitted from both laser diodes 30 and 31 is combined using beam splitter/combiner 32. The beam splitter 32 creates pump beam 34 and a probe beam 35 each comprising the two beams with frequencies $\omega_1$ and $\omega_2$.

The probe beam 35 is fed, via plain mirror 37, into optical delay line 36, which is used as a phase coupling/control means. In the optical delay line 36, the probe beam 35 is reflected off a cube mirror, which is used to reflect the light through 180°. The cube mirror is moveable such that the path length of the probe beam can be varied. Since the probe beam 35 has a known phase relationship to that of the THz radiation, this phase control/coupling means provides the detector 24 with a parameter corresponding to a phase input that can be varied relative to the source beam. Alternatively the optical delay could be positioned so that it varies the phase of the pump beam supplied to an input of the detector 24, with respect to the probe beam.

This phase control is required as the sample 20 introduces a time delay in the path of the pump beam. The delay is dependent on both the absorption coefficient and the refractive index of the sample. The frequency component of the probe beam must be in phase with a frequency component of the pump beam in order to obtain a detection signal. Variation of optical delay 16 allows the phase of the probe beam and/or pump beam to be swept with respect to the pump beam and/or probe beam and thus allows for measurement of the delay time of each frequency component which passes through the sample.

The pump beam 34, which comprises radiation with frequencies $\omega_1$ and $\omega_2$, irradiates the emitter 33. The pump beam impinges on the semiconductor emitter 33 on the part of its surface between the electrodes 38a and 38b, i.e. where the field is applied. The beating of the two visible or near-infrared lasers in the non-linear region of the semiconductor emitter between the two electrodes 38a and 38b results in the emission of THz radiation from the semiconductor emitter 33. The emitter 33 is provided with a lens (not shown), which may be of a hemispherical or other design, on its surface opposite to that of the surface with the electrodes, to allow the emission of a beam of THz radiation.

The emitted radiation is focussed onto the sample 20. The investigating technique illustrated gathers reflected THz radiation and the detector illustrated in FIG. 3 is a photoconductive detector. Both the irradiating technique and the detector are as described in relation to FIG. 1.

An advantage of the THz CW detecting apparatus over the THz pulsed detecting apparatus is that the CW apparatus can readily account for arbitrary changes in the THz path length, from the beam splitter to the detector. For instance, in pulsed detecting apparatus, the beam from the laser is split into a pump beam 13 and a probe beam 14. In order to achieve detection, the THz pulse 29 and probe beam from the laser must arrive at the detector at the same time. This simultaneous timing is achieved through the use of the variable delay 16. That is, the THz path length from the beam splitter to the THz generator to the detector via the sample is known or can be determined, and an appropriate delay added to the probe beam 14 so that it arrives at the detector at the same time. While this simultaneous timing can be controlled fairly easily in an experimental environment, for a practical implementation of a pulsed detection system this is more of a critical factor. For example, if during the investigation of a bag to determine if it contained explosives, the bag was moved relative to the measuring apparatus, the THz path length would suddenly change. This change would need to be compensated for using the delay line, which is not a simple matter.

This issue is addressed in CW investigating apparatus. In CW systems, a beam (cos ($\omega_1$t)) from a first laser 30 and a beam (cos $\omega_2$t) from a second laser 31 are combined to provide optical power at both the emitter and detector. This instantaneous optical power varies as (cos [($\omega_1-\omega_2$)t] cos [($\omega_1+\omega_2$)t]) including a term that varies at the sum frequency and a term that varies at the difference frequency. The sum frequency is not relevant, as neither the detector material itself, nor its metallic contacts respond this quickly. They can, however, follow the difference frequency.

Figure 8:
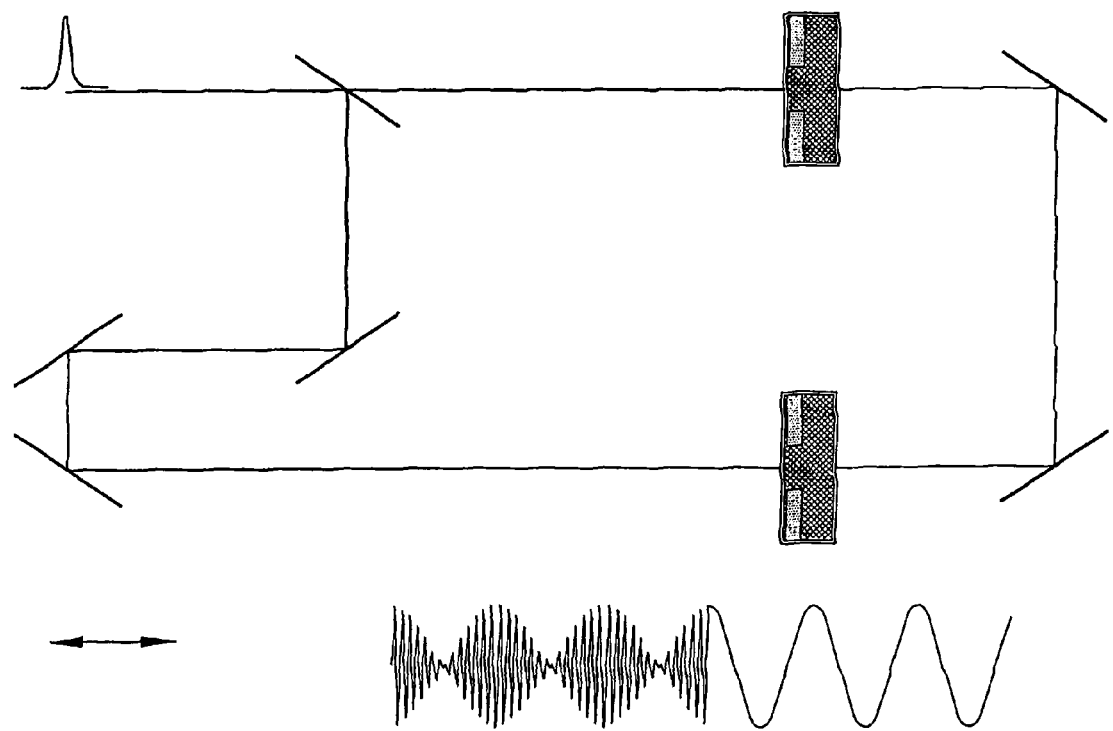
FIG. 8 illustrates a schematic of a CW arrangement and the phase relationship between the pump beam and the probe beam at the detector.

Therefore, in CW detection it is the difference frequency (cos [($\omega_1-\omega_2$)t]) component of the combined lasers, and the THz beam of the same frequency that need to arrive at the detector 24 in phase. FIG. 8 illustrates a simplified schematic of a CW detection apparatus and showing the difference frequency as an overtone arriving at the detector 24 in phase with the sinusoidal emitted THz frequency.

From the illustration of these two waves meeting at the detector 24 in FIG. 8 it is apparent that moving the delay line by one THz period sweeps the detection through a complete cycle and would result in the two waves still being in phase. Therefore, if the object being investigated moves in any way so as to change the THz path length, even dramatically, the most the delay line will need to be altered to recover maximum detection efficiency is ½ a THz period. This is typically at most a few millimetres, which is readily achievable.

In the detection of explosive materials, such as in an apparatus for the routine security screening of people, the arrangements in FIGS. 1 to 3 can adapted as required. For example, rather than irradiating a sample, the arrangements could be configured to focus on a region and irradiate whatever object or objects lie in that region.

The THz pulses detected at the detector can be analysed to provide various information about the irradiated object in the time and frequency domains. For example, time-of-flight measurements of radiation reflected off the rear surface of an object provides quasi-absorption information. In the frequency domain, transmittance, which is the ratio of transmitted to incident radiation at a particular frequency, is determined by the thickness and absorption coefficient of the irradiated object and absorbance is the logarithm of the inverse transmittance.

To provide signal intensity spectra, the detected THz pulse (which is a function of the optical delay) is Fourier transformed to yield a spectral function of frequency.

To illustrate the utility of the Terhertz investigating arrangements of FIGS. 1 to 3, FIGS. 4 to 7 show spectra obtained using the FIG. 2 apparatus to investigate a number of materials containing explosives in a controlled environment. The samples were held in an evacuated space to eliminate water absorption and the spectra were taken in transmission.

The materials characterised by this method can be separated into individual explosive chemicals, and explosives containing a either a combination of these, or the base ingredient plus other compounds. The measured individual explosives were:
 i) 2,4,6-Trinitrotoluene (TNT);
 ii) 1,3,5-Trinitro-1,3,5-triazacyclohexane (RDX); and
 iii) Pentaerythritol tetranitrate (PETN);
 iv) 1,3,5,7-Tetranitro-1,3,5,7-tetrazacyclooctane (HMX).

Figure 4:
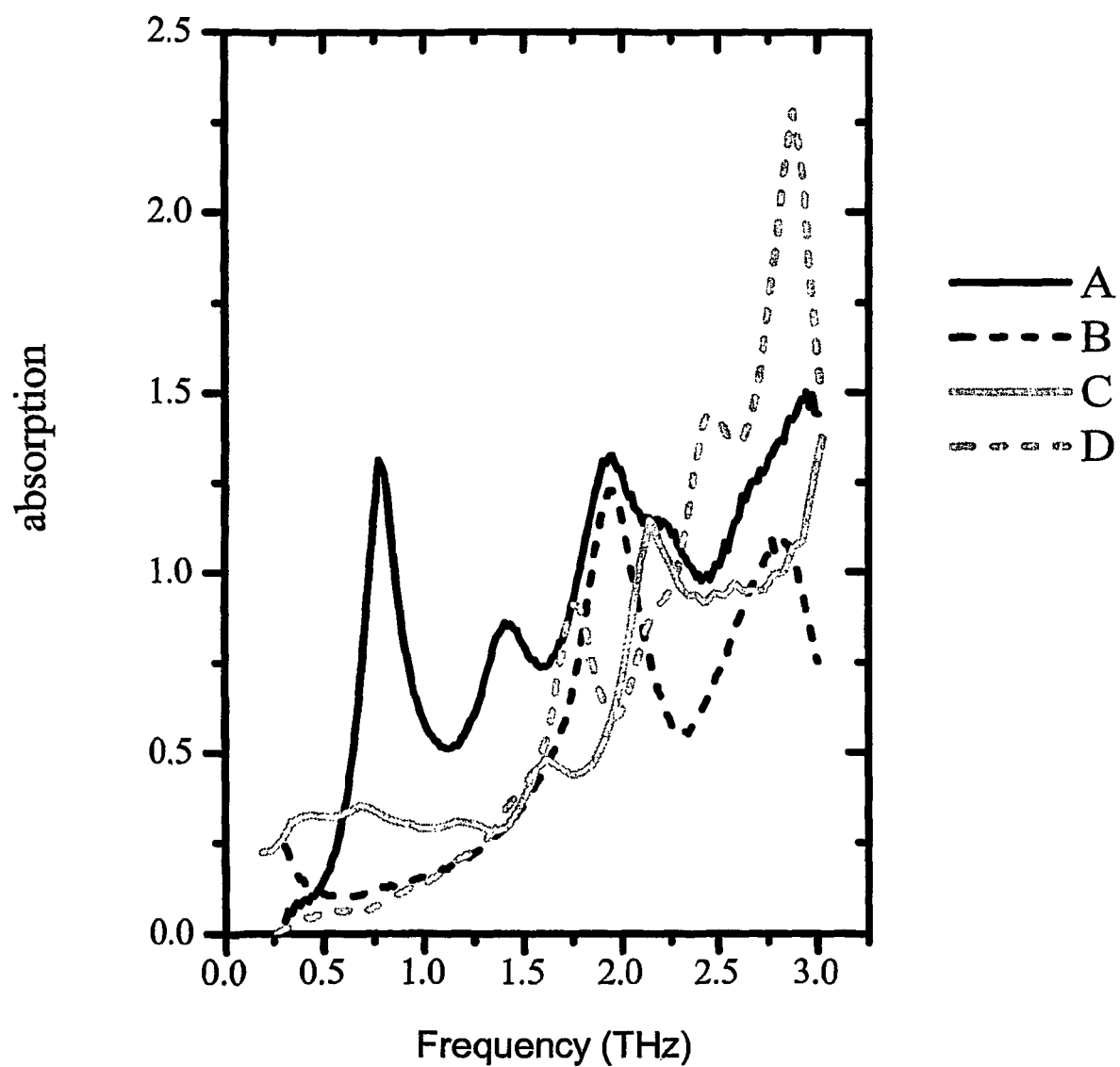
FIG. 4 illustrates transmission absorption spectra for four explosive compositions of different concentrations obtained using an embodiment of the present invention.

FIG. 4 is a comparative graph showing the transmission spectra of these individual explosive compositions. The samples of less than 100% purity were powders, and were prepared for measurement in tablet form by compression with polyethylene. Polyethylene has a flat spectral response in the frequency range 0-3 THz, and so the spectral features in FIG. 4 are those of the explosive component. The spectrum, labelled A, illustrates the absorption of the sample containing approximately 25% RDX. The absorption spectrum has quite marked and distinctive peaks at frequencies of approximately 0.75, 1.4, 1.95 and 2.9 THz. The peak at 1.95 THz is in fact a double peak, although this is not readily apparent in FIG. 4 in view of the resolution used.

The spectrum labelled B is for a composition of approximately 25% PETN and has two definite peaks at 1.95 and 2.8 THz. The spectrum labelled C is for a composition containing pure TNT. This composition has definite peaks at 1.6 and 2.15 THz with evidence of weaker spectral features between 0.25 and 1.25 THz. The remaining spectrum, labelled D, is for a composition containing approximately 25% HMX. This spectrum has definite peaks at 1.75, 2.45 and 2.9 THz.

Figure 5:
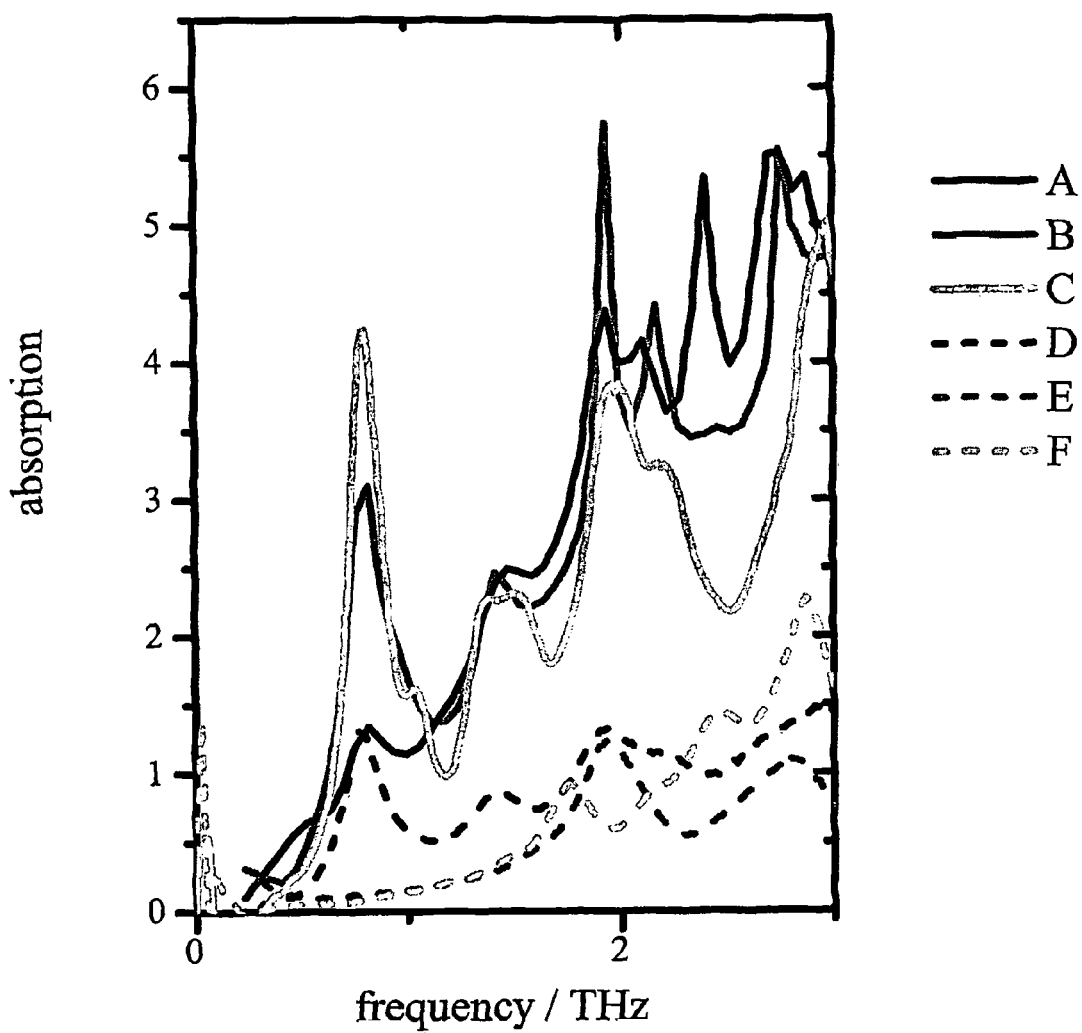
FIG. 5 illustrates transmission absorption spectra for a number of different explosive compositions obtained using an embodiment of the present invention.

FIG. 5 is another comparative graph, showing the transmission spectra of selected individual explosives—as appear also in FIG. 4—along with those from combined explosives. The combined explosives are those that are commonly used, typically representing military plastic explosives. These are as follows:
i) Semtex 40% RDX, 40% PETN, with the rest being plasticizers composed of poly(butadiene-styrene) and oil.
ii) PE-4 Also commonly known as C-4, contains 90% RDX, plus plasticizers composed of polyisobutylene, di(2-ethylhexyl)sebacate and fuel oil.
iii) SX-2 A military explosive which comes in thin sheet form, and contains 88.2% RDX, 8.2% polyisobutylene, 2.2% Di(2-ethylhexyl)Sebecate, and 1.4% polytetrofluoroethylene.

The spectra for Semtex, PE-4 and SX2 are labelled A, B and C respectively, and those for RDX, PETN and HMX are labelled D, E and F respectively. The spectra for D, E, and F correspond to the same spectra, marked A, B, and D respectively on FIG. 4, except with a different scale on the absorption axis.

Comparing the RDX spectra labelled D with the PE-4 spectra, labelled B, it is apparent that the PE-4 spectra has peaks at the same locations as the RDX spectra, but with much higher absorbancy, so that the peaks are more marked. This is also the case for the SX2 spectra, marked C. As both PE-4 and SX2 consist of approximately 90% RDX, this shows that the location of the peaks are due to fundamental properties of the explosive compositions. The higher absorbancy is considered to be mainly due to the larger grain size of the constituents of the PE-4 composition, which results in greater scattering and therefore greater absorption.

Comparing the Semtex spectrum, labelled A, with the individual spectra of its explosive constituents, PETN (labelled E) and RDX (labelled D) it is apparent that the peaks in the Semtex spectrum occur in the same regions as both of the PETN and RDX spectra, so that the Semtex spectrum is effectively the combination of both spectra. In the region of 1.8-2.0 THz, a double peak is clearly evident in the spectra of Semtex, PE-4 and SX2. This is due to a corresponding double peak in the RDX spectrum, although the double peak is less apparent in the RDX spectrum due to the resolution used in FIG. 4.

The presence of the HMX spectrum, F, in FIG. 5, is related to that of the Semtex, labelled A. We note that there is a peak in the semtex spectrum at 2.25 THz, which is not explained by the spectra of either RDX or PETN. However, RDX can be manufactured in one of two ways, one of which leaves the chemical with trace quantities of HMX, the other which can incorporate up to 9% of HMX as an impurity (REF "Forensic and Envoronmental detection of Explosives, J. Yinon, John Wiley and Sons Ltd (Chichester, England), 1999). HMX has a spectral feature at this frequency, and it is plausible therefore that the RDX present within the Semtex sample contained measurable quantities of HMX, whereas the pure RDX explosive did not.

These comparative graphs of FIGS. 4 and 5 show that Terahertz irradiation is able to produce spectra for explosive materials where the overall spectra is dependent upon fundamental properties of the material itself, such as the vibrational states of chemical bonds and molecules.

As an alternative to analysing spectra across the whole Terahertz range of interest it is also possible to identify materials by comparing spectral intensity ratios at predetermined frequencies. Turning again to FIG. 4, it can be seen that for the RDX spectrum, labelled A, it would be sufficient to measure the absorption at 0.75, 1.4 and 1.95 THz (the first three spectral peaks) in order to distinguish this substance from PETN (spectrum labelled B). Additionally measuring a fourth point at, say, approximately 1.1 THz—where there is no RDX peak—allows absolute verification of a peak in the absorption at 0.7 THz in RDX but not in PETN.

However, if the complete spectra is not available (and for example, the measurement at 1.1 THz is unavailable) then the materials can still be identified by calculating intensity ratios at the other frequencies since this allows comparison with known and expected ratios for both RDX and PETN. In this manner the presence of certain materials can be verified even if the complete spectra is not available.

Figure 6:
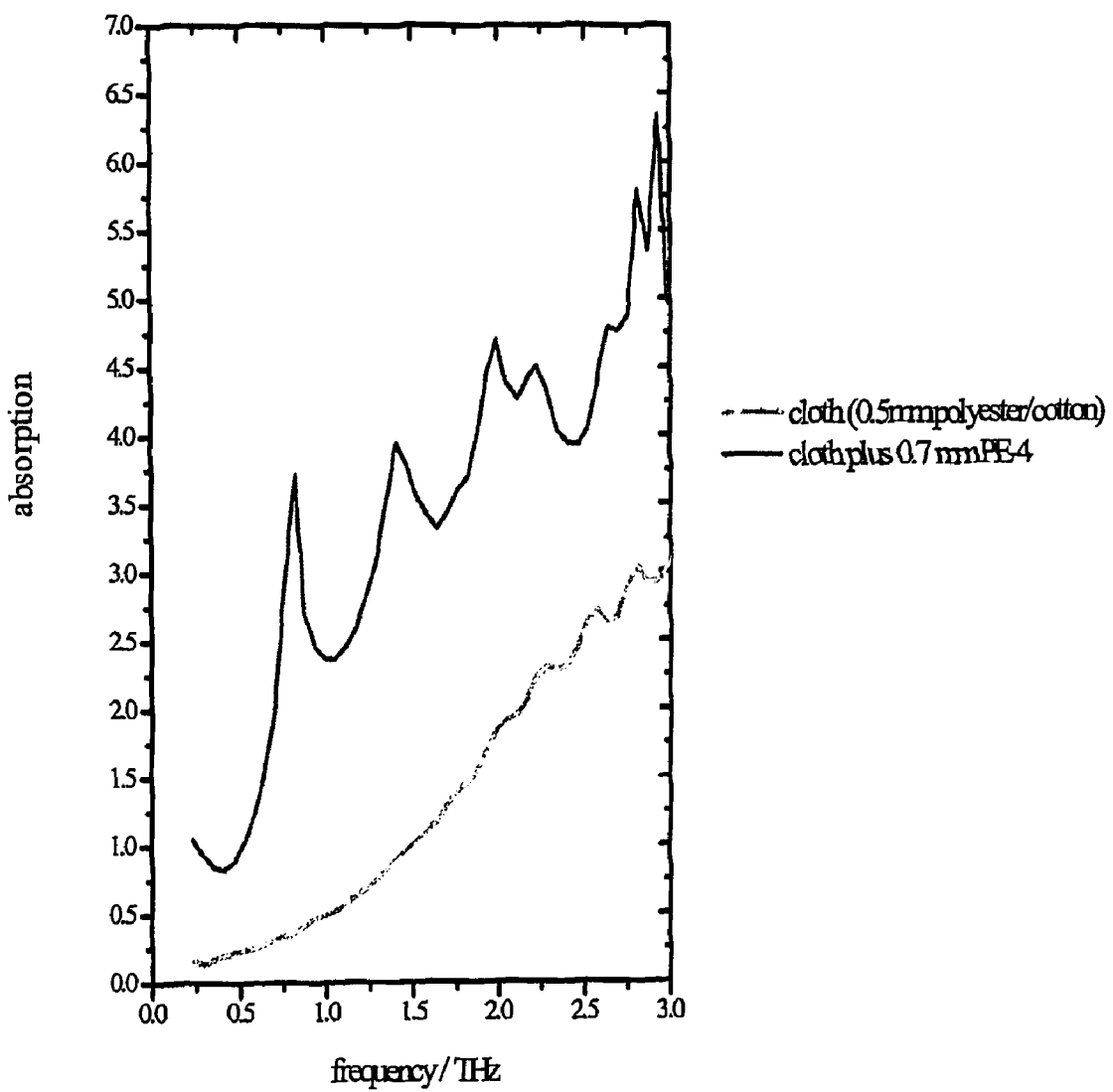
FIG. 6 illustrates transmission absorption spectra for an explosive composition, PE-4, and the same explosive composition covered by cloth.

With reference to FIG. 6, in order to further highlight features in a spectrum, the first derivative of the spectrum may be calculated and mapped. This is a key feature, as it allows unique features of an explosive material's spectrum to be highlighted from beneath materials such as cloth. In this regard, FIG. 6 compares the spectrum for a 0.5 mm thick piece of polyester/cotton cloth, being the lower, less absorptive, spectrum, against the spectrum for a piece of cloth combined with a 0.7 mm piece of PE-4 explosive.

The spectrum for the cloth alone has almost linear gradient. Taking the first derivative of this spectrum, would essentially result in a constant. As the cloth plus PE-4 spectrum can be considered as essentially the sum of the cloth spectrum and the PE-4 spectrum individually, by taking the first derivative of the combined spectrum, the effect of the cloth can be effectively removed.

Further, comparing the cloth and PE-4 spectrum in FIG. 6 with the PE-4 spectrum labelled A in FIG. 5 it is apparent that both spectra have peaks at the same frequencies, such as in the region of 0.8, 1.5, 2.0, 2.2 and 2.3 THz. This confirms that the cloth does not affect the ability to detect the fundamental properties of the underlying explosive.

Figure 7:
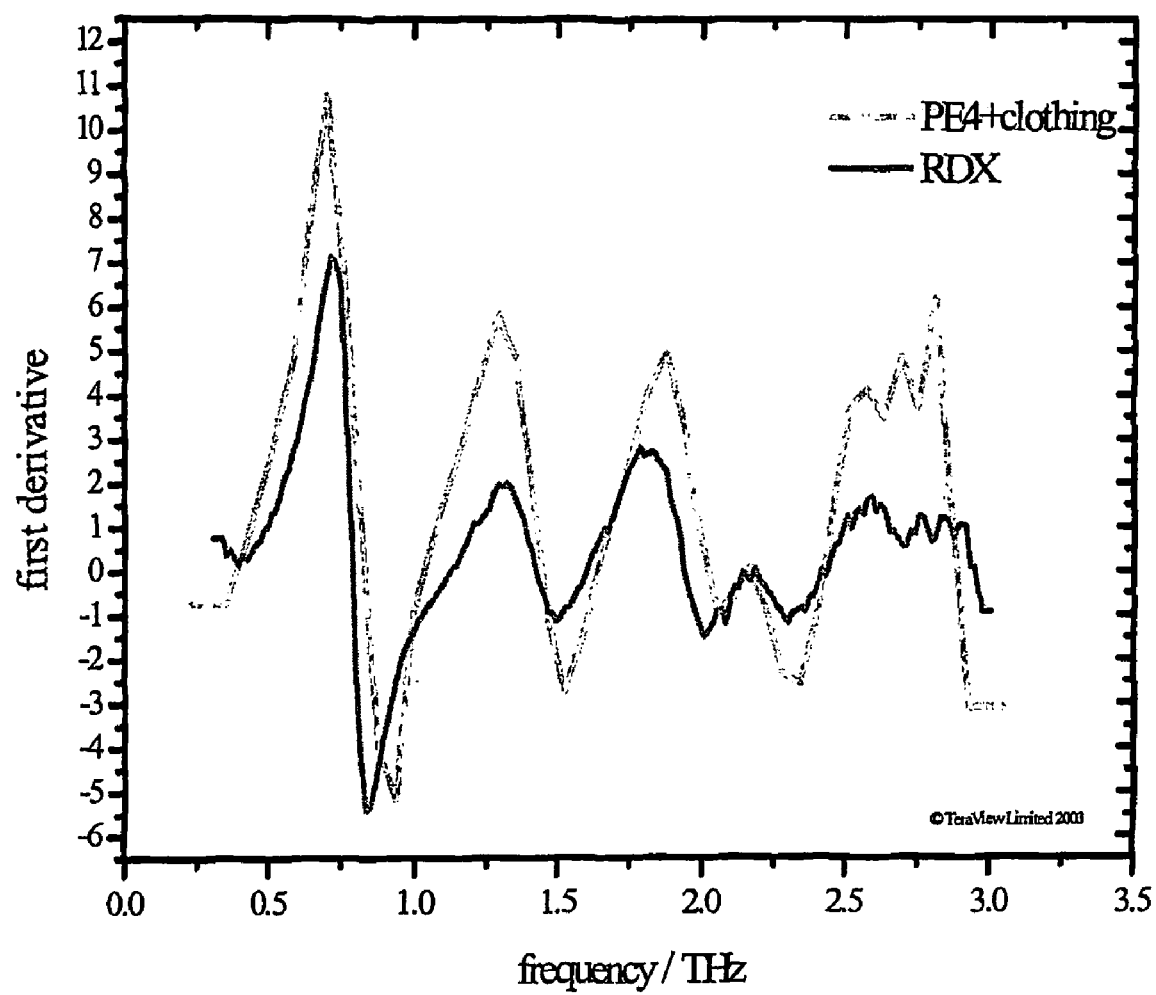
FIG. 7 illustrates the first derivative of the PE-4 covered by cloth spectra of FIG. 6 and compares that to the first derivative of RDX, being the main constituent of the PE-4.

Further referring to FIG. 7, the first derivative of the spectum for the cloth plus PE-4 combination of FIG. 6 is illustrated. This first derivative is compared with the first derivative of the spectrum of RDX alone (RDX is the main constituent of PE-4 (i.e. 90%)). This graph again shows peaks in the same regions, confirming the similarities in the fundamental properties in the spectra.

Figure 9:
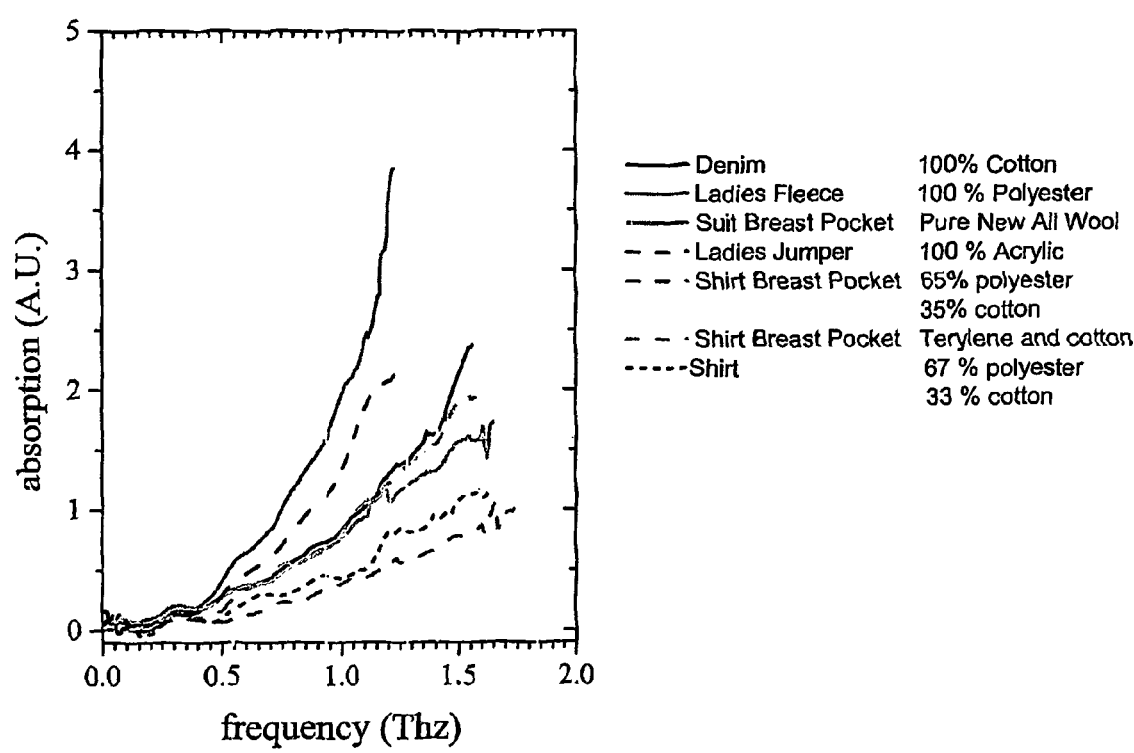
FIG. 9 illustrates transmission absorption spectra for various clothing materials.

Other types of clothing materials were also investigated and all showed the absorption background to rise with frequency, but in an essentially linear manner. These spectra are illustrated in FIG. 9. These spectra were obtained with a system that was not as fully optimised as the current system, so the system bandwidth was not ideal. Hence the measurements have been curtailed at about 1.5 THz. It is considered that the linearity will continue at higher frequencies with a fully optimised system. This is also supported by the spectra for a poly-cotton cloth in FIG. 6, which was obtained with a fully calibrated system and demonstrates substantial linearity through 3.0 THz.

Therefore, the contribution to the spectra from clothing can be essentially eliminated by obtaining first derivative spectra. Hence, this shows that even where an explosive is irradiated under a person's clothing, this technique can allow a spectrum of an explosive to be accurately obtained.

Therefore, once such spectra is obtained, the determination that an explosive material exists can be made by a detailed knowledge of the expected spectra. This may be achieved by comparing the ratios of the intensities measured at a number of different key indicative frequencies across the spectral range. This simplifies the analysis of the spectra required.

In terms of approaches that utilise CW to investigate an object, as CW is tunable but monochromatic, discrete measurements can be made at pre-determined key indicative frequencies in the process of determining whether or not an explosive is present. This approach is advantageous, as it means that broadband will not be necessary where a small number of key indicators exists, as the above spectra indeed indicate.

As well as using THz radiation in transmission to identify explosive materials, reflection spectroscopy is another approach which can be utilised.

Figure 10:
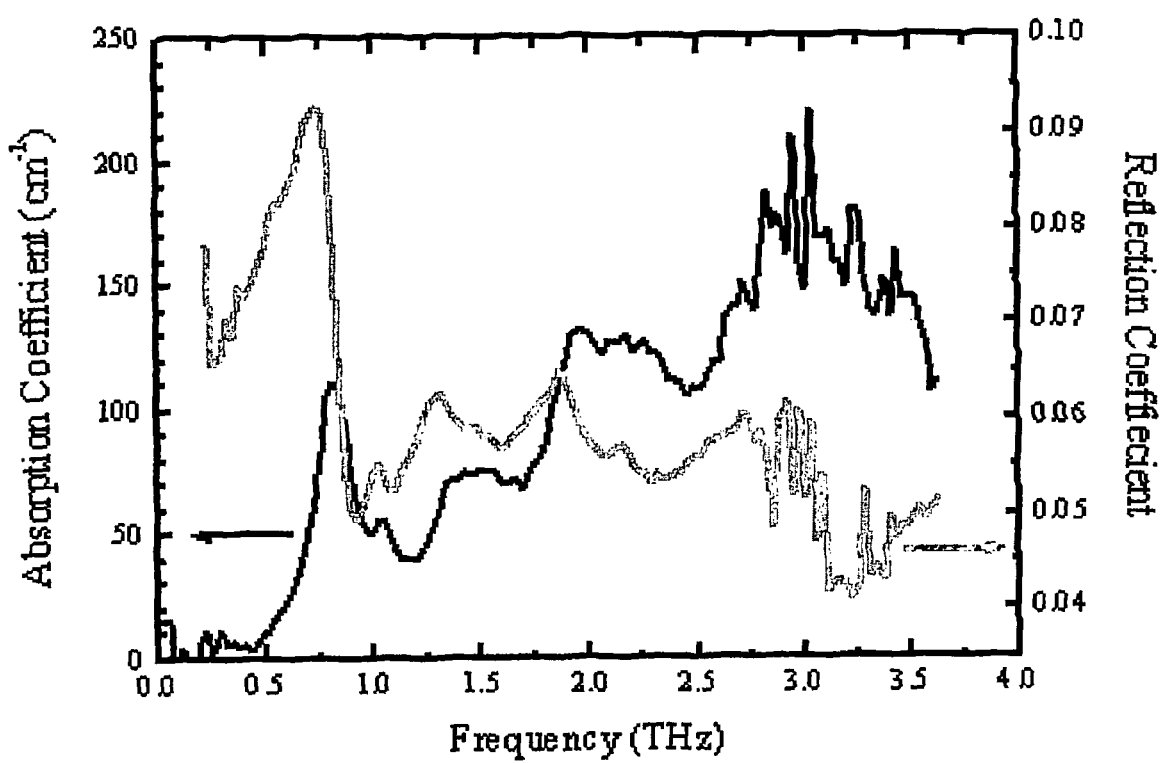
FIG. 10 illustrates a measured absorption spectrum for PE-4 and a corresponding mathematically calculated reflection spectrum.

As a general illustration that the unique spectral features visible in absorption are also manifested in reflection, well established mathematical formulae relating to absorption and reflection were utilised to produce the reflection spectrum for PE-4 illustrated in FIG. 10. The absorption spectrum for PE-4, which was measured using the apparatus of FIG. 2, is shown in black. The reflectance spectrum, shown in grey, was calculated from the measured absorption spectrum. This demonstrates that features in the absorption spectrum should also be evident in reflectance spectrum, and in many instances correspond with features in the absorption spectrum.

Figure 11:
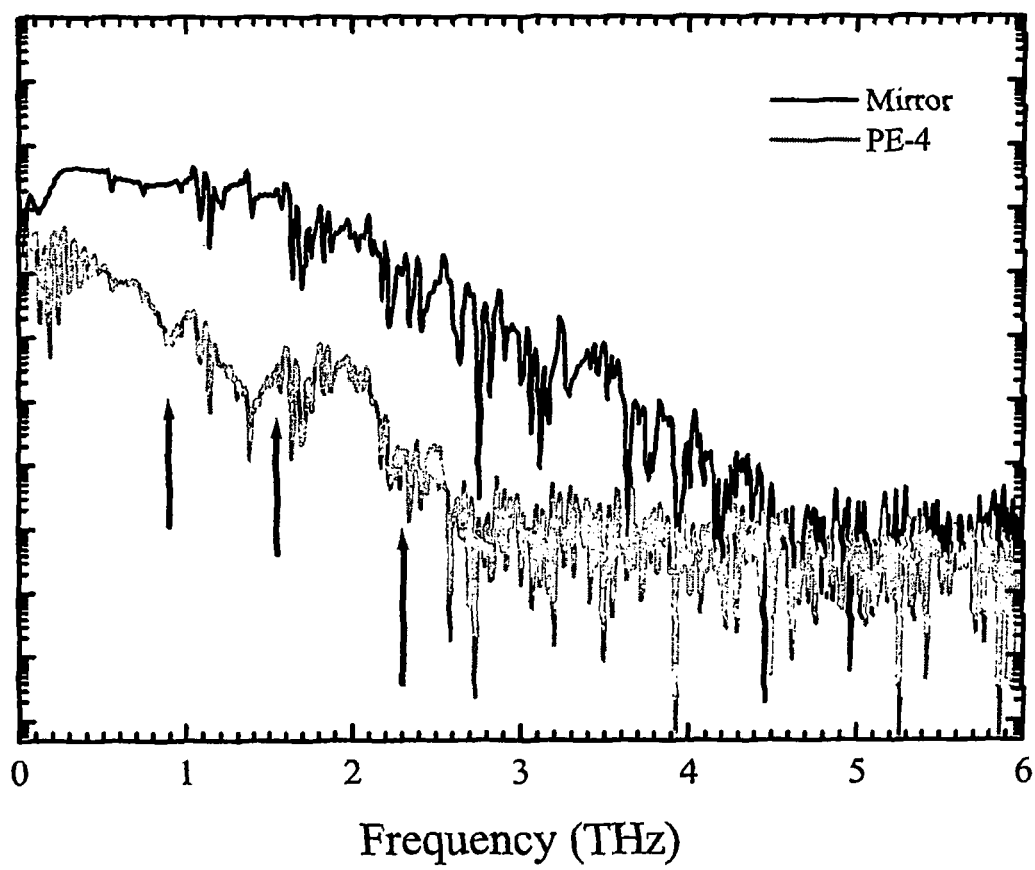
FIG. 11 illustrates reflectance power spectra for explosive material PE-4 and for a reference.

To support this mathematical calculation, FIG. 11 illustrates spectra measured from an apparatus of the type depicted in FIG. 1, which is a reflection THz imaging and spectroscopy apparatus, and in which the sample is held in a normal atmosphere. The upper curve is that from a mirror held at the focal plane, and provides a reference for the power spectrum of the apparatus. The lower curve is a measured reflectance power spectrum for PE-4.

The arrows point to the frequencies at which spectral features are expected, around 0.8, 1.5 and 2.3 THz. These expected spectral feature frequencies were calculated from the measured absorption spectrum of FIG. 10, and are also in close agreement with the features measured in the transmission spectrum shown in FIG. 5 (labelled A). The correlation of these frequencies with the observed dips in THz power in the reflectance power spectrum, particularly around 0.9 THz, illustrates that reflective spectroscopy, like transmissive spectroscopy, can be used to uniquely identify explosives.

The sharp features visible in this reflection spectrum for PE-4 (for example the complex of three dips at around 1.1-1.3 THz) are related to atmospheric water absorption. To properly view the fundamental features of the spectrum for the explosive material, it may be necessary to eliminate or at least minimise these water absorption effects.

With regard to the measurements presented in FIGS. 4 to 9, these were taken on an ideal apparatus, depicted in FIG. 2, which involves transmission through a vacuum. These measurements showed that THz transmission spectroscopy does produce spectra dependent upon fundamental properties of explosive materials. Where the same techniques are utilised for explosives detection performed through a real atmosphere, the spectra would include water absorption. Therefore, in a real atmosphere, it may be necessary to remove the effects of water absorption from the transmission spectrum or spectra obtained.

To illustrate the effects of water absorption, in FIG. 13, a measured THz power spectrum, measured using the transmission apparatus depicted in FIG. 2, but in the absence of any sample, is illustrated in black. This was also measured in the absence of air. The grey power spectrum represents a calculation of the expected spectrum, including this measured spectrum and adding the absorbing effects of a passage of the THz radiation through 5 m of air (The measured water absorption of air in this frequency range is presented in FIG. 12). Comparing this spectrum represented in grey with the spectrum in an evacuated environment, it is apparent that water vapour adversely affects the overall spectrum to a substantial degree.

Figure 12:
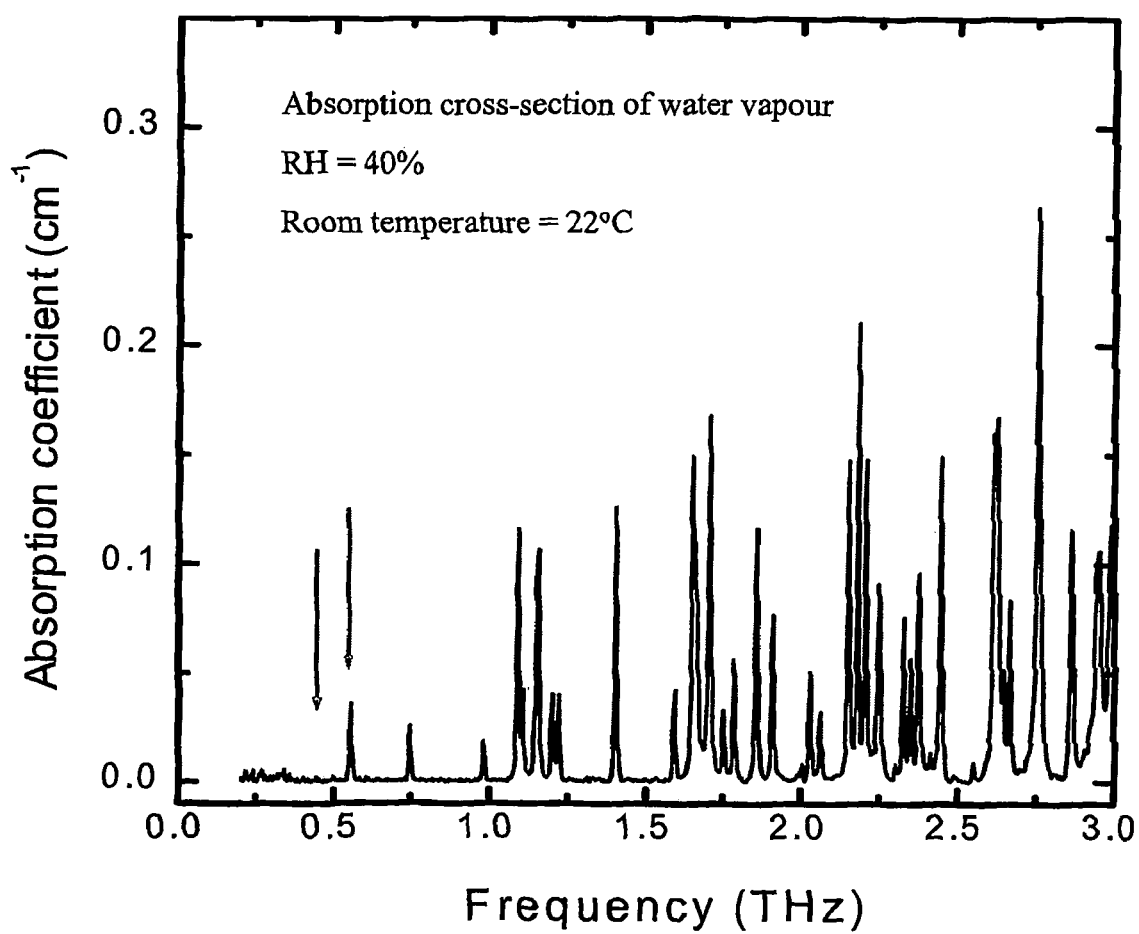
FIG. 12 illustrates the absorption spectrum for water vapour.

To extract the useful features of the explosive material from the power spectrum, one approach is to remove the water absorption effects. This will be discussed in more detail shortly. However, another approach is to utilise the well established absorption spectrum for water vapour, which is illustrated in FIG. 12. From this spectrum, a number of windows are evident, such as in the regions of 0.65, 0.9, 1.3, 1.5, 1.9 and 2.5 THz, where there are minimal effects of water absorption. Referring to the spectra in FIG. 12, it is also apparent that these windows exist in the grey spectrum of the explosive material under normal atmospheric conditions.

Therefore, it is possible to obtain spectra at these frequencies, which reflect the explosive material being analysed, without requiring the effects of water absorption to be countered. Referring again to FIG. 13, frequencies at which features indicative of Semtex and/or PE4 can be determined are indicated by dotted lines. A number of these frequencies correspond with these atmospheric water absorption windows. Therefore, a detector for identifying these explosives could obtain transmission or reflectance spectra and analyse the spectra at these frequencies, without requiring countermeasures for water absorption, and still be able to accurately detect features indicative of such explosives.

Where it is necessary to eliminate the adverse effects of water absorption, one approach involves mathematically removing the water absorption component from a spectrum. This could easily be achieved by measuring a known water absorption line (or lines) in a spectrum, and calculating the comparative absorption that would produce such a spectral feature. From this calculation, and from the fact that the water absorption lines within the measured spectrum of FIG. 12 are always present at known fixed ratios, it is possible to mathematically eliminate the water absorption effects across the whole range of the frequency spectrum.

For example, FIG. 12 represents the measured full spectrum from a pulsed THz experiment. With this knowledge it is only necessary to measure THz absorption at the two frequencies indicated by the two arrows. The ratio of these two spectral intensity measurements allows a complete water spectrum to be calculated.

Another approach relies on the sharpness of the water absorption lines. These have fundamentally lower linewidths than the features of a spectrum related to an explosive substance. That is, the features in an explosive substance spectrum have a greater FWHM (Full Width Half Maximum) interval than that of water vapour. Therefore, where the detection apparatus has a higher resolution than the linewidth of an explosive spectral feature, by reducing the system resolution, water absorption features will display a reduction in resolution, whereas features truly related to a substance's spectral resolution will not.

Such an approach is illustrated in FIG. 14, which illustrates a THz power spectrum obtained for PE-4. For pulsed methods, where the frequency power spectrum is determined from a Fourier transform of the measured THz pulse, the resolution of the frequency spectrum is related to the range of the pulse measurement. Therefore, by arbitrarily curtailing the data set of the pulse for the Fourier transform, the resolution of the frequency power spectrum is reduced. This is seen clearly in the FIG. 11, in which the data set (and hence resolution) is progressively reduced, from largest data set (highest resolution) for the bottom curve, to smallest data set (lowest resolution) at the top.

In particular, at approximately 1.4 THz, it can be seen that the sharp spectral feature, broadens dramatically as the resolution is decreased. From the absorption spectra for PE-4 in FIG. 5, labelled B, we know that PE-4 displays a spectra feature at approximately 1.4 THz. Hence, the broader reflectivity dip at 1.4 THz in FIG. 11 at the lowest resolution (top curve) is due to the explosive, with the sharp water absorption feature removed. This therefore shows that this is one approach of separating spectral features and minimising the effect of atmospheric water absorption.

Variations and additions are possible within the general inventive concept, as will be apparent to the person skilled in the art.

For instance, as an alternative to obtaining frequency spectra from reflection measurements, it is also possible to utilise time-of-flight measurements to determine whether an explosive material exists. In this regard, radiation reflected off the rear surface of an object provides quasi-absorption information. This is because the passage of the radiation through the object will provide a measurement relating to the absorption of the material.

Further, the beams may be delivered to the emitter, the detector and the irradiating apparatus by any means, including via fiber optics. Where a fiber optic delivery system is utilised, dispersion compensation schemes and appropriate focussing optics into and out of the fibers may be employed.

It is also possible for the skilled person to devise a detection apparatus which utilises both transmission and reflection spectra to determine the presence of spectral features indicative of an explosive material.

The invention claimed is:

1. A method of detecting an explosive material or composition, comprising:
   irradiating a sample comprising an object surrounded by a surrounding material with an optically-generated pulse of electromagnetic radiation, said pulse having a plurality of frequencies in the range from 100 GHz to 100 THz;
   detecting radiation transmitted and/or reflected from the object;
   adjusting the detected radiation signal to compensate for the effect of the surrounding material;
   differentiating the signal of the detected radiation to compensate for the effect of the surrounding material; and
   identifying one or more features of the detected radiation which are indicative of a known explosive material or composition.

2. The method of claim 1 wherein the identification of one or more feature comprises determining whether the detected radiation is indicative of a fundamental property of one or more explosive materials/compositions.

3. The method of claim 1 wherein identifying one or more features of the detected radiation comprises determining a frequency spectrum from the detected radiation.

4. The method of claim 3 further comprising analysing the frequency spectrum at predetermined frequencies to determine if features of known explosive materials/compositions are present.

5. The method of claim 1, further comprising obtaining a first derivative of the obtained spectra.

6. The method of claim 1 further comprising applying a measure to reduce water absorption effects in the detected radiation.

7. The method of claim 6 wherein the effects of water absorption are reduced by reducing the resolution in the analysis of the detected radiation.

8. The method of claim 1 wherein said explosive material or composition is covered with a member, said method further comprising compensating for the signal due to the member by differentiating the detected radiation.

9. The method of claim 8 wherein the signal is compensated for by obtaining the first derivative of a frequency spectrum of the detected radiation.

10. The method of claim 1 wherein identifying one or more features of the detected radiation comprises: obtaining a measure relating to the time-of-flight of the detected radiation reflected off a rear surface of the object;
    obtaining a measure relating to the absorption of the objection from the time-of-flight measure;
    determining whether the object is an explosive material from the absorption measure.

11. A method of detecting an explosive material, comprising:
    irradiating a sample comprising an object surrounded by a surrounding material with an optically-generated beam of substantially continuous electromagnetic radiation having a frequency in the range 100 GHz to 100 THz;
    detecting radiation transmitted and/or reflected from the object;
    adjusting the detected radiation signal to compensate for the effect of the surrounding material;
    differentiating the signal of the detected radiation to compensate for the effect of the surrounding material; and
    identifying one or more features of the detected radiation which are indicative of a known explosive material or composition.

12. The method of claim 11 wherein identifying one or more features of the detected radiation comprises obtaining a frequency spectrum at a number of predetermined frequencies and analyzing the spectra at the predetermined frequencies to determine if features of known explosive materials are present.

13. The method of claim 12 wherein identifying one or more features of the detected radiation comprises comparing the spectral intensity of the predetermined frequencies with expected intensities relating to one or more explosive materials/compositions.

14. The method of claim 12 wherein the analysis comprises calculating at least one ratio of spectral intensity at first and second predetermined frequencies and comparing with expected intensity ratios relating to one or more explosive materials.

15. The method of claim 14 wherein a plurality of intensity ratios are calculated for the spectral signature from a predetermined set of frequencies and are compared with expected intensity rations relating to one or more explosive materials.

16. The method of claim 12 wherein at least one of the predetermined frequencies correspond to a region of low water absorption.

17. The method of claim 11, further comprising:
    determining whether a reference beam at the detector is in phase with the detected radiation; and
    adjusting the detected radiation by at most a period to achieve an in-phase.

18. An explosive detection apparatus, comprising:
    an optically-driven emitter for directly irradiating a sample comprising an object surrounded by a surrounding material with a beam of substantially continuous electromagnetic radiation having a frequency in the range 100 GHz to 100 THz;
    means for detecting radiation transmitted and/or reflected from the object,
    analyser for adjusting and differentiating the detected radiation signal to compensate for the effect of the surrounding material and to determine if one or more predetermined features of an explosive material exists.

19. The apparatus of claim 18 wherein the analyser calculates a frequency spectrum from the detected radiation, and the apparatus further comprises a comparator for comparing the calculated spectrum with one or more known spectra of explosive materials/compositions to determine whether a likeness exists.

20. An explosive detection apparatus, comprising:
    an optically-driven emitter for directly irradiating a sample comprising an object surrounded by a surrounding material with a pulse of electromagnetic radiation, said pulse having a plurality of frequencies in the range from 100 GHz to 100 THz;
    means for detecting radiation transmitted and/or reflected from the object;
    analyser for adjusting and differentiating the detected radiation signal to compensate for the effect of the surrounding material and to determine if one or more predetermined features of an explosive material exists.

* * * * *